(12) United States Patent
Tatsumi et al.

(10) Patent No.: US 7,193,097 B2
(45) Date of Patent: Mar. 20, 2007

(54) METHOD OF PRODUCING A FATTY ACID ESTER

(75) Inventors: Nobuhiro Tatsumi, Wakayama (JP); Takanobu Katayama, Wakayama (JP); Osamu Tabata, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/899,076

(22) Filed: Jul. 27, 2004

(65) Prior Publication Data

US 2005/0033071 A1 Feb. 10, 2005

(30) Foreign Application Priority Data

Aug. 7, 2003 (JP) .............................. 2003-288477

(51) Int. Cl.
*C11C 1/00* (2006.01)
(52) U.S. Cl. ...................................... 554/167
(58) Field of Classification Search ................. 554/167
See application file for complete search history.

(56) References Cited

FOREIGN PATENT DOCUMENTS

| EP | 0200982 | 11/1986 |
|---|---|---|
| JP | 61-254255 | 11/1986 |
| JP | 2000-109883 | 4/2000 |
| JP | 2000-143586 | 5/2000 |
| JP | 2000-204392 | 7/2000 |
| JP | 2001-31991 | 2/2001 |

OTHER PUBLICATIONS

Yu et al., Biotechnology Prog., vol. 8, pp. 508-513, 1992.*
Central Pollution Control Board, Parivesh, pp. 1-4, "Biodiesel as Automobile, 4.0 Biodiesel Specifications".
K. Sakurai, et al., Oil Chemistry, vol. 19, No. 8, pp. 562-571, "Esterification and Interesterification", 1970.
B. Freedman, et al., Analysis of Soybean Oil by CGC, vol. 63, No. 10, pp. 1375-1380, "Transesterification Kinetics of Soybean Oil", 1986.

* cited by examiner

*Primary Examiner*—Deborah D. Carr
(74) *Attorney, Agent, or Firm*—Oblon, Spivak, McClelland, Maier & Neustadt, P.C.

(57) ABSTRACT

The present invention relates to a method of producing a fatty acid ester, including reacting fat and oil with an alcohol in the presence of at least one third component, wherein the third component is in a supercritical state or subcritical state under the condition of preventing a uniform phase from forming.

18 Claims, 2 Drawing Sheets

METHOD OF PRODUCING A FATTY ACID ESTER

FIELD OF THE INVENTION

The present invention relates to a method of producing a fatty acid ester from fat and oil and an alcohol.

BACKGROUND OF THE INVENTION

An alcoholysis reaction between fat and oil and an alcohol is known as a method of producing a fatty acid ester. This reaction is usually run using an alkali catalyst. There are, besides this reaction, an enzymatic reaction using lipase and a non-catalyst reaction run by bringing an alcohol into contact with fat and oil in a supercritical state or subcritical state. Methods of producing fatty acid esters through such reaction are disclosed in publications JP-A No. 2000-143586, JP-A No. 2001-31991, JP-A No. 2000-109883 and JP-A No. 2000-204392.

Fatty acid esters are generally used as industrial raw material and also have been used as biodiesel fuels in recent years. High purity is required for fatty acid esters used as industrial raw materials or biodiesel fuels. It is pointed out that the total amount of glycerol (total amount of glycerin, monoglyceride, diglyceride and triglyceride) left in a fatty acid ester is a factor that directly affects productivity in industrial applications or a factor that induces engine stains in biodiesel fuel applications (ASTM PS121 Biodiesel for B20).

The reaction between fat and oil and an alcohol not only produces a fatty acid ester but also glycerin. The reaction between fat and oil and an alcohol is considered to be naturally controlled by thermodynamic equilibrium (Oil Chemistry, Vol. 19, No. 8). Therefore, the solubility of glycerin in the fatty acid ester affects the reaction yield, that is, the purity of the fatty acid ester.

To state this reaction in more detail, the reaction is the step-equilibrium reaction of triglyceride which is a major component of fat and oil, the reaction being given by the following reaction formula as described in J. Am. Oil Chem. Soc., 63, pp 1375–1380 (1986).

In the formula, TG represents a triglyceride, DG represents a diglyceride, MG represents a monoglyceride, Alc. represents an alcohol, Gly represents glycerin and FAE represents a fatty acid ester.

SUMMARY OF THE INVENTION

The present invention relates to a method of producing a fatty acid ester, including reacting fat and oil with an alcohol in the presence of a third component, wherein the third component is in a supercritical state or subcritical state under the condition of preventing a uniform phase from forming.

Figure 1:
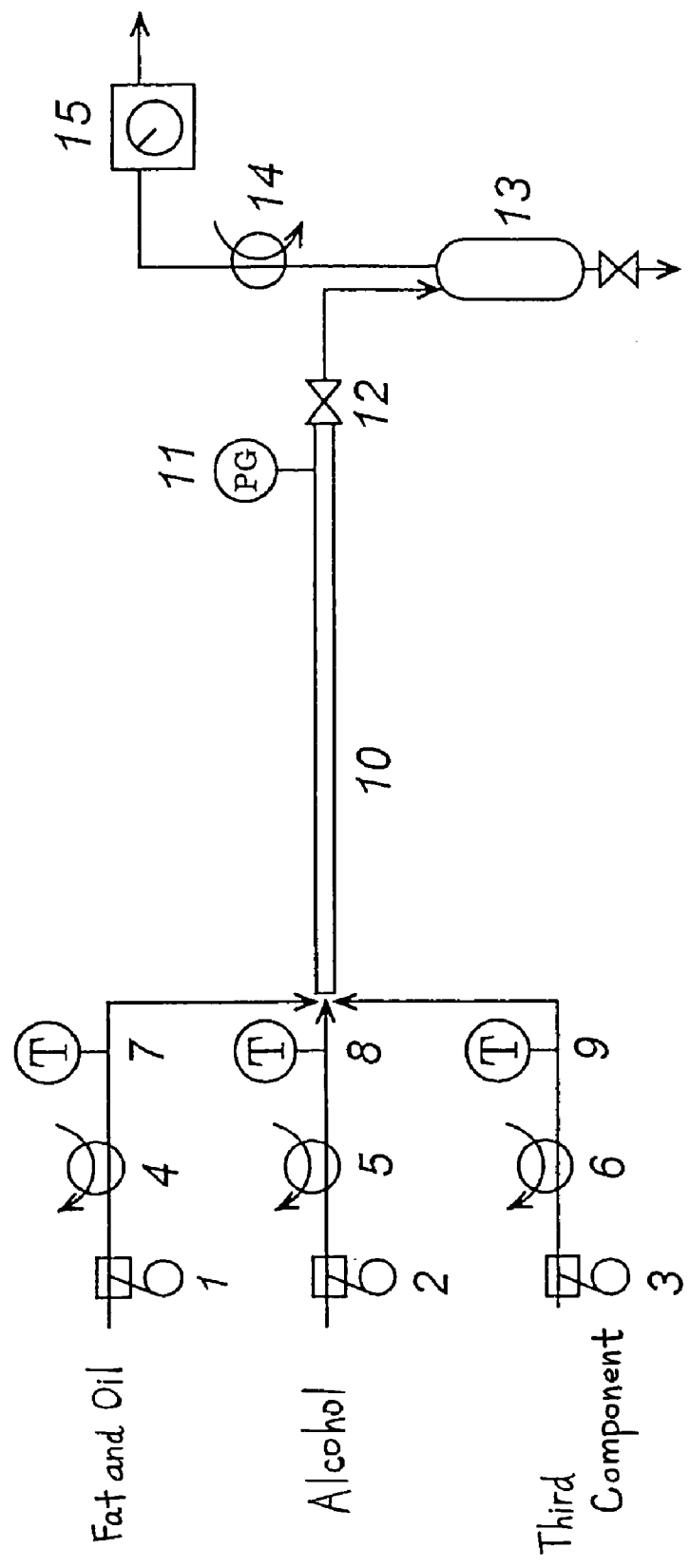
FIG. 1 is a schematic view showing one example of a continuous flow system reactor used in the present invention.

The symbols in these figures are explained as follows.
1: Fat and oil feed pump
2: Alcohol feed pump
3: Third component feed pump
4, 5, 6: Heater
7, 8. 9: Temperature regulator
10: Reactor
11: Pressure gauge
12: Pressure regulating valve
13: Receiver
14: Cooler
15: Gas flow meter
16: Pressure regulator
17: Pressure regulator

DETAILED DESCRIPTION OF THE INVENTION

In the disclosure of the above patent publication, no fatty acid ester having sufficiently high purity has been obtained yet at a high yield.

In the step-equilibrium reaction described above under the background of the invention, the glycerin produced is a material which is slightly soluble in a fatty acid ester. The residual amount of a monoglyceride and diglyceride which are reaction intermediates can be minimized by making the fatty acid ester have extremely low solubility. Therefore, it is a significant technical advantage in decreasing the concentration of glycerin in a reaction field. In the background technologies, it is difficult to separate glycerin, monoglyceride and diglyceride from each other, which complicates the process. In these background technologies, a fatty acid ester, glycerin, unreacted raw materials and reaction intermediates (monoglyceride and diglyceride) are remaining in the reaction mixture after the reaction and must be therefore refined and separated to a purity suitable for each use. As refining methods, operations such as extraction and distillation are required. As the purity of the fatty acid ester is decreased, the refining process becomes more complicated and requires heavy equipment.

The present invention relates to a method of producing a high purity fatty acid ester having a significant decrease in unreacted fat and oil and reaction intermediates, from fat and oil and an alcohol in a very simple method.

The inventors of the present invention have found that the solubility of glycerin in oil can be decreased and a high purity fatty acid ester can be simply produced at a high yield by reacting fat and oil with an alcohol in a specified condition.

The present invention relates to a method of producing a high purity fatty acid ester extremely decreased in the content of unreacted fat and oil and reaction intermediates from fat and oil and an alcohol in a very simple method.

According to the present invention, a high quality fatty acid ester can be produced at a high yield from fat and oil and an alcohol in a simple method. Because the resulting fatty acid ester contains less glycerol and can be produced efficiently at a low cost, it is useful as industrial raw materials and fuels.

(Fat and Oil)

Examples of the fat and oil used in the present invention include natural vegetable fat and oil and animal fat and oil. Examples of the vegetable fat and oil include rape seed oil, soybean oil, coconut oil, palm oil, palm kernel oil, sunflower oil, sesame oil, corn oil, safflower oil and linseed oil and examples of the animal fat and oil include fish oil, beef tallow and lard, though the fat and oil used in the present invention are not limited to these examples. Also, wastes of these fat and oil and wastes of these edible oils may also be used as the raw material.

(Alcohol)

The alcohol used in the present invention is preferably an aliphatic alcohol having 1 to 10 carbon atoms, though no particular limitation is imposed thereon. Fatty acid esters used as diesel fuels or industrial raw materials are preferably high quality lower alkyl esters. From this point of view, the alcohol is more preferably a lower alcohol having about 1 to 5 carbon atoms such as methanol, ethanol and propanol. Further, methanol is even more preferable from the viewpoint of cost and easiness of recovery.

In the present invention, the ratio by mol of the alcohol to the fat and oil is preferably 3 to 400, more preferably 10 to 150, even more preferably 15 to 100. When the ratio is 3 or more, the amount of the alcohol reaches the stoichiometrically required amount, the reaction can be completed and the residual amount of a diglyceride and monoglyceride decreases. Also, when the ratio is 400 or less, the cost required to recover excess alcohols can be suppressed.

(Third Component)

In the present invention, the third component means components other than the raw materials, reaction intermediates and products (triglyceride, diglyceride, monoglyceride, glycerin, alcohol and fatty acid ester). When this third component exists in the condition under which it is put in a subcritical or supercritical state, the reaction system does not form a uniform phase. Also, as the third component, those which can decrease the solubility of glycerin in oil are preferable.

The third component used in the present invention is preferably carbon dioxide or a hydrocarbon having 1 to 12 carbon atoms and more preferably carbon dioxide and hydrocarbons having 3 to 6 carbon atoms such as propane, butane, pentane and hexane.

Also, "solubility parameter (SP value)" of the third component may be adopted as a standard for selecting the third component. For example, a material having a small SP value may be selected to decrease the solubility of glycerin in oil because the SP value of glycerin is as large as 33.8 [(Mpa)$^{1/2}$]. Specifically, the third component is preferably those having a SP value of 21 or less, more preferably those having a SP value of 19 or less and even more preferably a SP value of 17 or less. Although there is no limitation to the lower limit of the SP value, the third component is preferably those having a SP value of 6 or more. Examples of compounds having such a SP value include propane, butane, pentane and hexane. In the present invention, at least one third component maybe used.

The SP value is described in, for example publications such as Polymer Handbook, 3rd edition (J. Barndup & E. H. Immergwt). Also, the SP value can be simply estimated by the group contribution method of Fedor.

In the present invention, the amount of the third component to the 1 mol of fat and oil is preferably 300 mols or less, more preferably 200 mols or less and even more preferably 100 mols or less because if the third component is added in a large amount, it cost to recover and if the third component is reused by circulating it in a continuous flow system, it costs for circulating machines, pipes, reactors and the like, though the amount of cost differs depending on the effect of decreasing the solubility of glycerin in oil. Also, the amount of the third component to the 1 mol of fat and oil is preferably 0.1 mol or more, more preferably 1 mol or more and even more preferably 5 mols or more from the viewpoint of decreasing the solubility of glycerin.

(Method of Producing a Fatty Acid Ester)

In the present invention, no particular limitation is imposed on the reaction system between the fat and oil and the alcohol. The reaction may be run in either a batch system or a continuous flow system. Also, the reaction may be run in the presence of no catalyst or by adding a catalyst or using a fixed bed prepared by packing and fixing a catalyst. In this case, any catalyst may be used without any particular limitation insofar as it has alcoholysis reaction activity. Examples of the catalyst include sodium carbonate and sodium bicarbonate as described in the publication of JP-A No. 61-254255, crystalline titanium aluminum silicate, crystalline titanium aluminum silicate and amorphous titanium silicate as described in EP0623581B1 and corresponding zirconium compounds.

In the present invention, the condition under which the reaction is run by adding the third component is a condition under which the third component is put in a subcritical or supercritical state. The use of the third component put in a subcritical or supercritical state makes it possible to separate glycerin efficiently and to run the reaction.

Specifically, the condition under which the third component is put in a supercritical or subcritical state is preferably a condition satisfying both the following equations (I) and (II).

$$0.9 \times Tc < T \quad (I)$$

$$0.9 \times Pc < P \quad (II)$$

where:

T: reaction temperature [K], Tc: supercritical temperature of the third component [K], P: reaction pressure [MPa] and Pc: critical pressure [MPa] of the third component.

For example in the case of using carbon dioxide as the third component, the reaction is run at a temperature of 273.8 K or more since the supercritical temperature of carbon dioxide is 304.2 K. Also, the reaction is run under a pressure of 6.6 MPa or more because the critical pressure of carbon dioxide is 7.38 MPa. When pentane is used as the third component, the reaction is run at a temperature of 422.6 K or more since the supercritical temperature of pentane is 469.6 K. Also, the reaction is run under a pressure of 3.0 MPa or more because the critical pressure of pentane is 3.37 MPa.

There is no particular limitation to the upper limit of the reaction temperature. The reaction temperature may be determined in consideration of product qualities, process and utility costs and operation costs and is preferably 400° C. or less and more preferably 350° C. or less. Also, the upper limit of the reaction pressure is preferably 70 MPa or less and more preferably 30 MPa or less from the perspective of both the equipment and operation costs, though there is no particular limitation as to the upper limit.

Moreover, in order to improve reaction yield by separating glycerin positively from the oil phase, it is demanded of the reaction product not to form a homogenous phase as the operation condition. Namely, it is necessary to design the temperature, pressure condition, amount of the alcohol to be used and amount of the third component to be added to satisfy the condition under which no uniform phase is formed. More specifically, the operation is carried out at a temperature not higher than the critical temperature of the reaction mixture. Alternatively it is carried out at a pressure not higher than the critical pressure of the mixture. The critical temperature and critical pressure differ depending on the molar ratio of the alcohol (to the fat and oil) and the amount of the third component to be added.

As to the selection of the condition preventing the formation of a uniform phase, the condition can be calculated by a commercially available phase equilibrium calculation software. Examples of the commercially available software which may be utilized include PE2000 (Technishe Universitat Hamburg-Harburg), Prode Properties (PROD) and Aspen Plus (aspentech). Also, the condition can be confirmed experimentally by measuring phase equilibrium using a pressure vessel.

Figure 2:
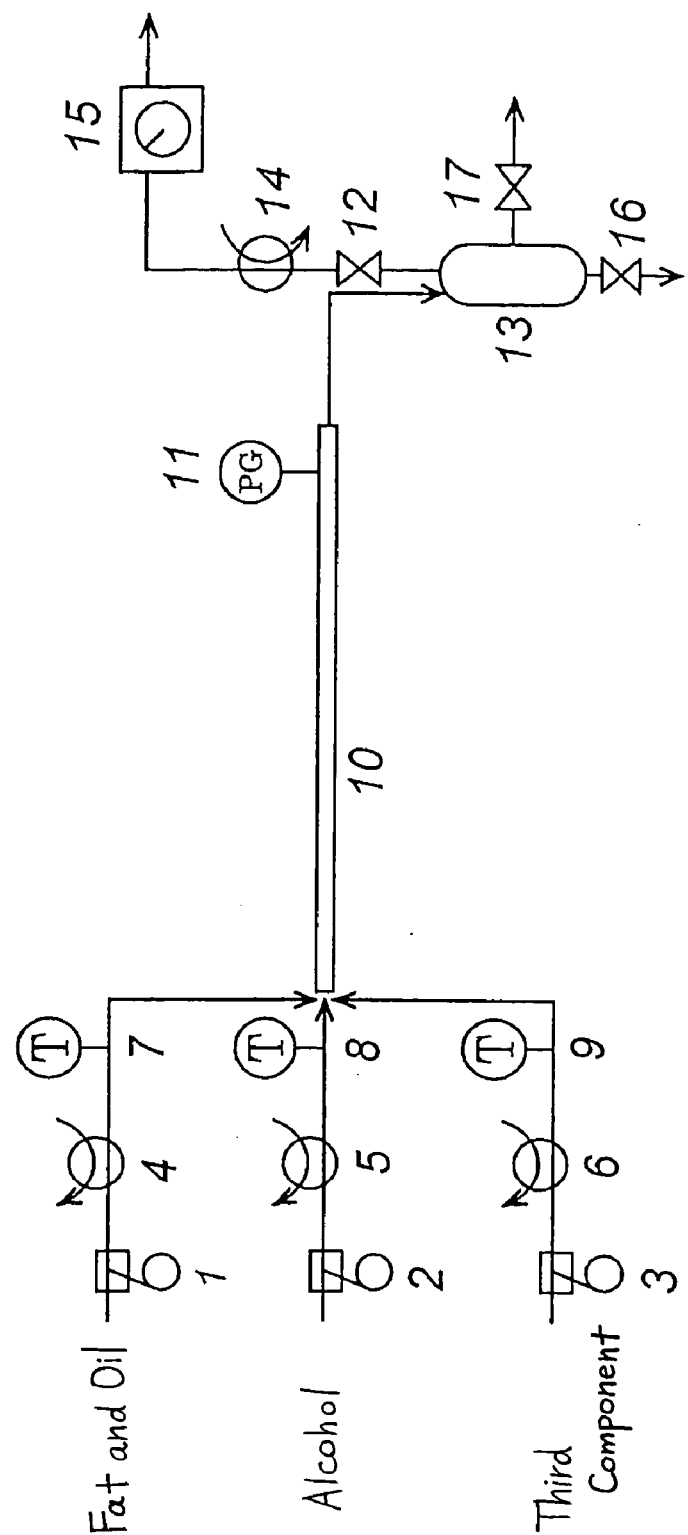
FIG. 2 is a schematic view showing another example of a continuous flow system reactor used in the present invention.

The production method of the present invention will be explained with reference to the drawings. FIG. 1 is a schematic view showing one example of a continuous flow system reactor used in the present invention. FIG. 2 is a schematic view showing another example of a continuous flow system reactor used in the present invention.

In the reactor shown in FIG. 1, the fat and oil, the alcohol and the third component which are the raw materials are respectively supplied to a reactor 10 by feed pumps 1, 2 and 3. At this time, these raw materials are heated to a desired temperature by heaters 4, 5 and 6 in advance. Also, the reactor may be provided with a temperature gauge installed to measure the reaction temperature and also with temperature regulators 7, 8 and 9 installed to maintain an even temperature. The reaction pressure is regulated constantly by a pressure regulating valve 12 disposed at the outlet of the reactor and the reaction product is withdrawn continuously. The withdrawn reaction product including the unreacted alcohol and third component is stored in a receiver 13 wherein the unreacted alcohol is stored in the receiver 13 by cooling it in a cooler 14. Also, when the third component is gas under a normal temperature and pressure condition, the flow rate of the third component may be measured by a gas flow meter 15.

The reactor 10 may be installed either horizontally or vertically. Also, as to a method of supplying the raw materials, these raw materials may be supplied either in the upward or downward direction.

The liquid space velocity based on the fat and oil in the reactor is preferably designed to be 0.05 to 100/Hr. However, it may be determined appropriately based on equipment costs, reaction condition and reaction activity and is not limited to the above range.

The third component can be reused by circulating it. In the case of reusing by circulation, a typical gas circulator or the like may be used when the third component is used in the form of a gas. Also, the reacted gas is once cooled according to the need to recover the target product and the unreacted product contained in the gas and then supplied to the circulating machine. Or, the gas may be cooled to condense perfectly and the obtained liquid may be supplied again to the reactor 10.

In this reaction, a fatty acid ester which is the target material is generated and also glycerin is generated along with the progress of the reaction. At this time, the added third component works to decrease the solubility of glycerin in the oil and glycerin is separated from the oil. This allows the reaction to proceed more in a positive direction and therefore, the reactions for decreasing monoglycerides, diglycerides and triglycerides further proceed. Namely, the reaction yield of the fatty acid ester can be improved.

In the reactor shown in FIG. 2, the receiver 13 is made to have a pressure proof structure and system pressure is controlled at the outlet of the receiver 13 by pressure regulating valves 12, 16 and 17 to thereby separate a high purity fatty acid ester as a reaction product from glycerin by each valve. In this case, the content of glycerin in the fatty acid ester can be significantly decreased by the action of the third component, which is more effective because the subsequent process of purifying the fatty acid ester can be simplified.

EXAMPLES

The following examples further describe and demonstrate embodiments of the present invention. The examples are given solely for the purpose of illustration and are not to be construed as limitations of the present invention.

Example 1

7.5 g/Hr of refined palm kernel oil, 7.8 g/Hr of methanol and 33.9 g/Hr of carbon dioxide as the third component were fed to a tubular reactor (inside diameter: 0.004 m, length: 4.0 m and internal volume: 50 mL). The reaction temperature was kept at 300° C. (573 K) and the pressure was adjusted to 13 MPa by a valve installed at the exit of the reactor to withdraw the reaction product constantly. The resulting reaction product was transferred to a separating funnel and then washed twice with 80° C. warm water. The oil phase was subjected to dehydration treatment using sodium sulfate anhydride. The oil obtained after the dehydration treatment was made into a trimethylsilylated product, which was then subjected to a gas chromatography analyzer (HP-6890, manufactured by Hewlett Packard, Column DB-WAX) for composition analysis. The reaction condition and the oil composition after the reaction are shown in Table 1.

Comparative Example 1

The reaction was run in the same method as in Example 1 except that carbon dioxide was not supplied and the oil composition obtained after the reaction was finished was analyzed in the same manner as in Example 1. The reaction condition and the oil composition after the reaction are shown in Table 1.

TABLE 1

| | | Example 1 | Comparative example 1 |
|---|---|---|---|
| Methanol/palm kernel oil (mol ratio) | | 20 | 20 |
| carbon dioxide/palm kernel oil (mol ratio) | | 71 | — |
| Reaction temperature [K] | | 573 | 573 |
| Reaction pressure [MPa] | | 13 | 13 |
| Liquid space velosity of palm kernel oil (LHSV) | | 0.2 | 0.2 |
| Oil composition after reaction | TG | 0.1 | 0.0 |
| | DG | 0.2 | 0.3 |
| | MG | 2.1 | 3.0 |
| | ME* | 97.7 | 96.7 |

*Palm kernel oil fatty acid methyl ester

Catalyst Production Example 147 g of 85% phosphoric acid (manufactured by Katayama Chemical, Inc.), 49.5 g of ethylphosphonic acid (manufactured by Nippon Kagaku Kogyo (K.K.)) and 563 g of aluminum nitrate nonahydrate (manufactured by Katayama Chemical, Inc.) were dissolved in 5 L of ion exchange water. The solution was adjusted to pH=5 by adding aqueous 10% ammonia dropwise to the solution at 35° C. over 3 hours to obtain a precipitate. The obtained precipitate was subjected to filtration and the precipitate was washed with water repeatedly until the electroconductivity of the suspension became 1 mS/cm. The resulting washed cake was dried at 110° C. overnight and then crushed to a size of 0.25 mm or less to obtain a phosphorous-containing metal salt powder.

17.5 g (in which ignition loss content until the temperature became 250° C.: 2.5 g) of the phosphorous-containing acid metal salt powder was mixed sufficiently with 7.6 g of zirconium hydroxide (R zirconium hydroxide manufactured by DAIICHI KIGENSO KAGAKU KOGYO CO., LTD., 40% as zirconia), 0.15 g of methyl cellulose (manufactured by Shin-Etsu Chemical Co., Ltd.) and 5.0 g of titania sol (manufactured by Ishihara Techno Corp., 30% of titania is contained, stabilized by nitric acid). 8.3 g of water was further added to the mixture, which was then kneaded. The kneaded cake was molded by extruding the cake from a hole of 1.7 mm diameter under a pressure load of about 3 MPa, followed by baking at 320° C. to obtain catalyst 1.

Example 2

70 cc of the catalyst 1 prepared in Catalyst Production Example was filled in a fixed-bed type reactor (inside diameter: 0.013 m and length: 0.83 m). 6.5 g/Hr of refined palm kernel oil, 5.5 g/Hr of methanol (manufactured by Kishida Kagaku (K.K.), first class) and 15.5 g/Hr of pentane as the third component were fed to the fixed-bed reactor. The reaction temperature was kept at 200° C. (473 K) and the pressure was adjusted to 5 MPa by a valve installed at the exit of the reactor to withdraw the reaction product constantly. The resulting reaction product was transferred to a separating funnel and then washed twice with 80° C. warm water. The oil phase was subjected to dehydration treatment using sodium sulfate anhydride. The composition of the oil obtained after the dehydration treatment was analyzed in the same manner as in Example 1. The reaction condition and the oil composition after the reaction are shown in Table 2.

Comparative Example 2

The reaction was run in the same method as in Example 2 except that pentane was not supplied and the oil composition obtained after the reaction was finished was analyzed in the same manner as in Example 2. The reaction condition and the oil composition after the reaction are shown in Table 2.

Comparative Example 3

The reaction was run in the same manner as in Comparative Example 2 except that the supply rate of the raw materials was doubled. Specifically, 13 g/Hr of refined palm kernel oil and 11 g/Hr of methanol (manufactured by Kishida Kagaku (K.K.), first class) were fed to the fixed-bed reactor. The oil composition obtained after the reaction was finished was analyzed in the same manner as in Example 1. The reaction condition and the oil composition after the reaction are shown in Table 2.

It is considered from the results of Comparative Examples 2 and 3 shown in Table 2 that these reactions almost reach equilibrium.

TABLE 2

| | | Example 2 | Comparative example 2 | Comparative example 3 |
|---|---|---|---|---|
| Methanol/palm kenel oil (mole ratio) | | 20 | 20 | 20 |
| Pentane/Palm kernel oil (mole ratio) | | 25 | — | — |
| Reaction temperature [K] | | 473 | 473 | 473 |
| Reaction pressure [MPa] | | 5 | 5 | 5 |
| Liquid space velocity of palm kernel oil (LHSV) | | 0.1 | 0.1 | 0.2 |
| Oil composition after reaction | TG | 0.1 | 0.0 | 0.0 |
| | DG | 0.1 | 0.2 | 0.2 |
| | MG | 1.6 | 2.9 | 3.0 |
| | ME* | 98.2 | 96.9 | 96.8 |

*Palm kernel oil fatty acid methyl ester

As is clear from the results of Examples and Comparative Examples shown in Tables 1 and 2 that the amount of monoglyceride (MG) decreases in all Examples than in Comparative Examples and it is therefore considered that the concentration of glycerin (Gly) in the reaction field is reduced from the viewpoint of reaction equilibrium. Therefore, it is judged that no uniform phase is formed in the reaction of the present invention. Also, the method of the present invention makes it possible to decrease unreacted raw materials and reaction intermediates and a fatty acid ester having a higher quality can be therefore obtained.

The invention claimed is:

1. A nonenzymatic process of producing fatty acid ester, comprising:
   reacting fat and oil with an alcohol;
   wherein the nonenzymatic process occurs in the presence of at least one supercritical or subcritical solvent wherein the said solvent is selected from the group consisting of carbon dioxide and hydrocarbons having 1 to 12 carbon atoms.

2. The method according to claim 1, wherein the solvent is present in an amount that ranges from 0.1 to 300 mols based on 1 mol of fat and oil.

3. The method according to claim 1, wherein the solvent is present in an amount that ranges from 1 to 200 mols based on 1 mol of fat and oil.

4. The method according to claim 1, wherein the solvent is present in an amount that ranges from 5 to 100 mols based on 1 mol of fat and oil.

5. The method according to claim 1, wherein the mole ratio of alcohol to fat and oil ranges from 3 to 400.

6. The method according to claim 1, wherein the mole ratio of alcohol to fat and oil ranges from 15 to 100.

7. The method according to claim 1, which further comprises preventing the solvent from forming a uniform phase.

8. The method according to claim 1, wherein the solvent is selected from the group consisting of propane, butane, pentane, and hexane.

9. The method according to claim 1, wherein the solvent is propane.

10. The method according to claim 1, wherein the solvent is butane.

11. The method according to claim 1, wherein the solvent is pentane.

12. The method according to claim 1, wherein the solvent is hexane.

13. The method according to claim 1, wherein the reacting occurs in the presence of a catalyst selected from the group consisting of sodium carbonate; sodium bicarbonate; tita nium aluminum sulfate; and a salt containing titanium, zirconium, and phosphorous.

14. The method according to claim 1, wherein the reacting occurs in the presence of a salt containing titanium, zirconium, and phosphorous.

15. The method according to claim 1, wherein the reacting occurs at a temperature of the solvent carbon dioxide 300° C.

16. The method according to claim 1, wherein the reacting occurs at a temperature of wherein the solvent is pentane 200° C.

17. The method according to claim 1, wherein the fat and oil is at least one fat and oil selected from the group consisting of rape seed oil, soybean oil, coconut oil, palm oil, palm kernel oil, sunflower oil, sesame oil, corn oil, safflower oil, linseed oil, fish oil, beef tallow, and beef lard.

18. The method according to claim 1, wherein the alcohol is selected from the group consisting of methanol, ethanol, and propanol.

* * * * *